(12) United States Patent
Allenby et al.

(10) Patent No.: US 11,166,646 B2
(45) Date of Patent: Nov. 9, 2021

(54) SYSTEMS AND METHODS FOR MEDICAL PROCEDURE CONFIRMATION

(71) Applicant: Intuitive Surgical Operations Inc., Sunnyvale, CA (US)

(72) Inventors: Christopher Allenby, Sunnyvale, CA (US); Prashant Chopra, Sunnyvale, CA (US); John A. Cole, Hollister, CA (US)

( * ) Notice: Subject to any disclaimer, the term of this patent is extended or adjusted under 35 U.S.C. 154(b) by 1470 days.

(21) Appl. No.: 14/910,578

(22) PCT Filed: Aug. 12, 2014

(86) PCT No.: PCT/US2014/050729
§ 371 (c)(1),
(2) Date: Feb. 5, 2016

(87) PCT Pub. No.: WO2015/023671
PCT Pub. Date: Feb. 19, 2015

(65) Prior Publication Data
US 2016/0192860 A1    Jul. 7, 2016

Related U.S. Application Data

(60) Provisional application No. 61/866,356, filed on Aug. 15, 2013.

(51) Int. Cl.
*A61B 5/06*        (2006.01)
*A61B 10/02*       (2006.01)
(Continued)

(52) U.S. Cl.
CPC .............. *A61B 5/064* (2013.01); *A61B 10/02* (2013.01); *A61B 10/04* (2013.01);
(Continued)

(58) Field of Classification Search
CPC ......... A61B 5/064; A61B 10/02; A61B 10/04; A61B 2034/2051; A61B 2034/2061;
(Continued)

(56) References Cited

U.S. PATENT DOCUMENTS 6,336,904 B1    1/2002   Nikolchev
6,375,615 B1    4/2002   Flaherty et al.
(Continued)

FOREIGN PATENT DOCUMENTS

CN    1788692 A      6/2006
CN    101518466 A    9/2009
(Continued)

OTHER PUBLICATIONS

Mao et al. 2008 Med. Phys. 35:1942-1949 (Year: 2008).*
(Continued)

*Primary Examiner* — Michael J Tsai
*Assistant Examiner* — Patrick M Mehl
(74) *Attorney, Agent, or Firm* — Haynes and Boone, LLP

(57) ABSTRACT

A method comprises advancing a medical instrument and a catheter toward a target tissue within a patient anatomy. The instrument includes a distal sheath marker and is slidably received within the catheter. The distal sheath marker includes a channel and an identification feature. A portion of the instrument is slidably received within the channel. The method further comprises depositing the distal sheath marker at a location at or near the target. The distal sheath marker indicates a farthest advancement point of the instrument within the patient anatomy. The method further comprises: after depositing the distal sheath marker, withdrawing the instrument away from the target; determining an orientation of the distal sheath marker based on the identification feature; and, after withdrawing the instrument, using the location and orientation of the deposited distal sheath
(Continued)

marker to determine a trajectory of a distal end of the instrument at or near the target.

18 Claims, 7 Drawing Sheets

(51) Int. Cl.
*A61B 10/04* (2006.01)
*A61B 90/00* (2016.01)
*A61B 18/14* (2006.01)
*A61B 34/20* (2016.01)

(52) U.S. Cl.
CPC ... *A61B 18/1492* (2013.01); *A61B 2034/2051* (2016.02); *A61B 2034/2061* (2016.02); *A61B 2090/392* (2016.02); *A61B 2090/3908* (2016.02); *A61B 2090/3929* (2016.02); *A61B 2090/3933* (2016.02); *A61B 2090/3941* (2016.02); *A61B 2090/3966* (2016.02); *A61B 2090/3975* (2016.02); *A61B 2090/3983* (2016.02); *A61B 2090/3987* (2016.02)

(58) Field of Classification Search
CPC ........ A61B 2090/3929; A61B 18/1492; A61B 2090/3975; A61B 2090/3941; A61B 2090/3908; A61B 2090/3933; A61B 2090/3983; A61B 2090/3966; A61B 2090/3987; A61B 2090/392
See application file for complete search history.

(56) References Cited

U.S. PATENT DOCUMENTS

| | | | |
|---|---|---|---|
| 6,380,732 B1 | 4/2002 | Gilboa | |
| 6,389,187 B1 | 5/2002 | Greenaway et al. | |
| 6,994,712 B1* | 2/2006 | Fisher | A61B 90/39 |
| | | | 128/899 |
| 7,648,517 B2 | 1/2010 | Makower et al. | |
| 7,930,065 B2 | 4/2011 | Larkin et al. | |
| 8,398,596 B2* | 3/2013 | Field | A61M 5/178 |
| | | | 604/164.5 |
| 2001/0049502 A1* | 12/2001 | Chen | A61N 5/062 |
| | | | 604/167.06 |
| 2002/0058057 A1* | 5/2002 | Kaplan | A61M 36/14 |
| | | | 424/426 |
| 2002/0188196 A1* | 12/2002 | Burbank | A61B 6/00 |
| | | | 600/431 |
| 2004/0204670 A1* | 10/2004 | Nita et al. | A61B 17/22 |
| | | | 604/22 |
| 2005/0038355 A1 | 2/2005 | Gellman et al. | |
| 2005/0288722 A1 | 12/2005 | Eigler et al. | |
| 2006/0013523 A1 | 1/2006 | Childlers et al. | |
| 2006/0064006 A1 | 3/2006 | Strommer et al. | |
| 2008/0212082 A1 | 9/2008 | Froggatt et al. | |
| 2008/0260637 A1* | 10/2008 | Dickman | A61K 51/08 |
| | | | 424/1.69 |
| 2011/0021888 A1* | 1/2011 | Sing et al. | A61B 5/05 |
| | | | 600/302 |
| 2011/0061659 A1* | 3/2011 | Cruzada et al. | A61F 6/06 |
| | | | 128/831 |
| 2011/0184280 A1 | 7/2011 | Jones et al. | |
| 2011/0190662 A1* | 8/2011 | McWeeney | A61B 10/02 |
| | | | 600/567 |
| 2012/0289777 A1 | 11/2012 | Chopra et al. | |
| 2013/0079628 A1* | 3/2013 | Groszmann | A61B 6/12 |
| | | | 600/424 |

FOREIGN PATENT DOCUMENTS

| | | | | |
|---|---|---|---|---|
| CN | 102470013 A | | 5/2012 | |
| EP | 1302172 A1 | | 4/2003 | |
| EP | 1889572 A2 | | 2/2008 | |
| JP | 2006500991 A | | 1/2006 | |
| WO | WO-9729682 A1 | | 8/1997 | |
| WO | WO-0162135 A2 | | 8/2001 | |
| WO | WO-03011161 A1 | | 2/2003 | |
| WO | WO-2007035798 A2 | | 3/2007 | |
| WO | WO2012024085 A2 * | | 2/2012 | ............ A61M 36/04 |
| WO | WO-2012024085 A2 | | 2/2012 | |

OTHER PUBLICATIONS

International Search Report and Written Opinion for Application No. PCT/US2014/050729, dated Nov. 19, 2014, 17 pages.

International Preliminary Report on Patentability for Application No. PCT/US2014/050729, dated Feb. 25, 2016, 6 pages.

VERTUT, Jean and Phillipe Coiffet, Robot Technology: Teleoperation and Robotics Evolution and Development. English translation, Prentice-Hall, Inc. Inglewood Cliffs, NJ, USA 1986, vol. 3A, 332 pages.

Extended European Search Report for Application No. 14836614.9, dated Dec. 5, 2016, 7 pages.

\* cited by examiner

SYSTEMS AND METHODS FOR MEDICAL PROCEDURE CONFIRMATION

CROSS-REFERENCE TO RELATED APPLICATIONS

This application claims the benefit of International Patent Application No. PCT/US2014/050729 (filed Aug. 12, 2014); which claims priority from U.S. Patent Application No. 61/866,356 (filed Aug. 15, 2013); which are incorporated by reference herein in their entireties.

FIELD

The disclosure is directed to systems and methods for conducting a minimally invasive surgical procedure, and more particularly to systems and methods for confirming if a target of the minimally invasive surgical procedure has been reached.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians insert medical devices to reach a target tissue location. Medical devices include surgical instruments, such as therapeutic and diagnostic instruments, and other devices that may be temporarily or permanently implanted in the body. For some procedures, a minimally invasive medical device may navigate natural or surgically-created passageways in an anatomical system to reach the target tissue location. For example, a minimally invasive medical device may navigate natural passageways in the lungs, the colon, the intestines, the kidneys, the heart, the circulatory system, or the like. Some minimally invasive medical devices may be teleoperated or otherwise operated with computer assistance.

Minimally invasive medical procedures often require extreme precision, but traditional methods for confirming whether a procedure has been successfully completed may be inadequate. For example, when conducting a biopsy on sub-centimeter sized nodules, a clinician may be unable to quickly and accurately determine whether a diagnostic instrument (e.g., a biopsy instrument) successfully biopsied the target tissue. Systems and methods are needed to confirm that minimally invasive medical procedures, such as biopsies, have been successfully performed.

SUMMARY

Various embodiments are summarized by the claims that follow the description.

In one embodiment, a method comprises advancing a surgical instrument toward a target tissue. The surgical instrument includes a marker that is deposited at a location at or near the target tissue. After depositing the marker, the surgical instrument is withdrawn away from the target tissue. After withdrawing the surgical instrument, the location of the deposited marker is used to determine a trajectory of a distal end of the surgical instrument at or near the target tissue.

In another embodiment, a system comprises an elongated instrument and a trajectory indication device. The trajectory indication device is configured to indicate a trajectory of a distal end of the elongated instrument at or near a target tissue in a patient anatomy. The trajectory indication device includes a marker removable from the elongated instrument for deposit in a location at or near the target tissue.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of aspects of the invention, numerous specific details are set forth in order to provide a thorough understanding of the disclosed embodiments. It will be obvious to one skilled in the art, however, that the embodiments of this disclosure may be practiced without these specific details. In other instances well-known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates (i.e., sway, heave, and surge)). As used herein, the term "orientation" refers to the rotational placement of an object or a portion of an object in three-dimensional space (e.g., three degrees of rotational freedom around Cartesian X, Y, Z coordinates (i.e., pitch, yaw, roll)). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object. And as used herein, degrees of freedom refers to mechanical degrees of freedom that change an object's position and orientation—other mechanical degrees of freedom, such as grip action around a fulcrum or the motion of a push button, will be specifically discussed as necessary.

During a minimally invasive medical procedure, such as a biopsy, accuracy may be evaluated by assessing the trajectory of the biopsy instrument. As will be described in detail in this disclosure, one or markers may be deposited in the area of the biopsied tissue during the procedure. The marker may be imaged or otherwise sensed to convey instrument trajectory information to a clinician, confirming whether the target tissue was successfully accessed by the biopsy instrument.

Figure 1:
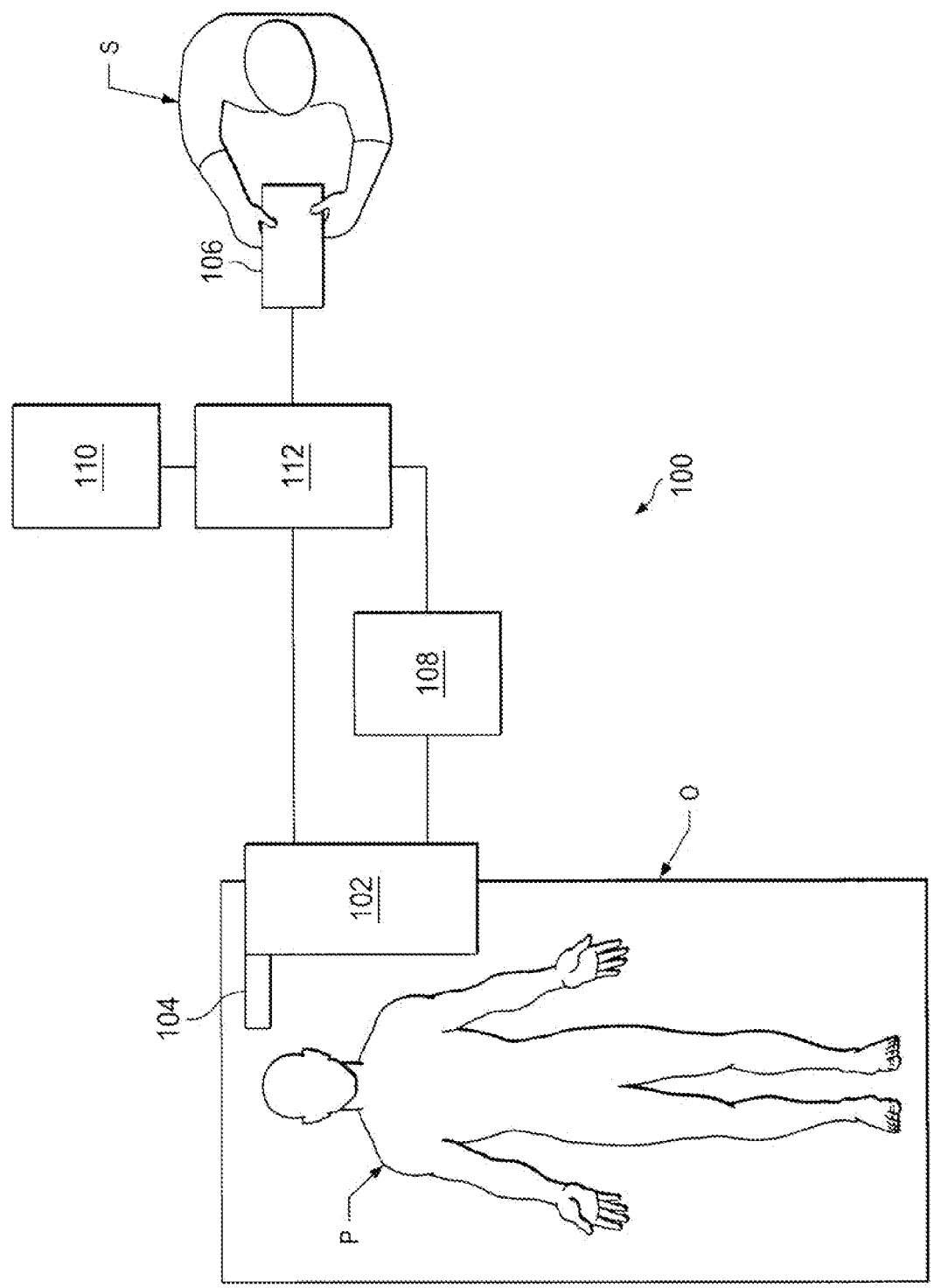
FIG. 1 is a teleoperational medical system, in accordance with an embodiment of the present disclosure.

According to various embodiments, medical procedures, such as biopsy procedures, may be performed using a teleoperational system to guide instrument delivery. Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or a sub-procedure. In still other alternative embodiments, a fully automated medical system, under the full control of a computer programmed to perform the procedure or a sub-procedure, may be used to perform procedures or sub-procedures.

As shown in FIG. 1, the teleoperational medical system 100 generally includes a teleoperational assembly 102 mounted to or near an operating table O on which a patient P is positioned. A medical instrument system 104 is operably coupled to the teleoperational assembly 102. An operator input system 106 allows a surgeon or other type of clinician S to view images of or representing the surgical site and to control the operation of the medical instrument system 104.

The operator input system 106 may be located at a surgeon's console, which is usually located in the same room as operating table O. It should be understood, however, that the surgeon S can be located in a different room or a completely different building from the patient P. Operator input system 106 generally includes one or more control device(s) for controlling the medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with at least the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of motors that drive inputs on the medical instrument system 104. These motors move in response to commands from the control system (e.g., control system 112). The motors include drive systems which when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

Alternatively or additionally, display system 110 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four-dimensional (including e.g., time based or velocity based information) images and associated image data sets for reproducing the images.

In some embodiments, the display system 110 may display a virtual visualization image in which the actual location of the medical instrument is registered (e.g., dynamically referenced) with preoperative or concurrent images to present the surgeon with a virtual image of the internal surgical site at the location of the tip of the medical instrument.

In other embodiments, the display system 110 may display a virtual visualization image in which the actual location of the medical instrument is registered with prior images (including preoperatively recorded images) or concurrent images to present the surgeon with a virtual image of a medical instrument at the surgical site. An image of a portion of the medical instrument system 104 may be superimposed on the virtual image to assist the surgeon controlling the medical instrument.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery"), which is incorporated by reference herein in its entirety, discloses one such system.

The teleoperational medical system 100 may further include optional operation and support systems (not shown) such as illumination systems to provide illumination for internal imaging, steering control systems for one or more portions of the inserted medical device, and suction and/or irrigation systems for use at a surgical site. In alternative embodiments, the teleoperational system may include more than one teleoperational assembly and/or more than one operator input system. The exact number of manipulator assemblies will depend on the surgical procedure and the space constraints within the operating room, among other factors. Multiple operator input systems may be collocated, or they may be positioned in separate locations. Multiple operator input systems allow more than one operator to control one or more manipulator assemblies in various combinations.

Figure 2:
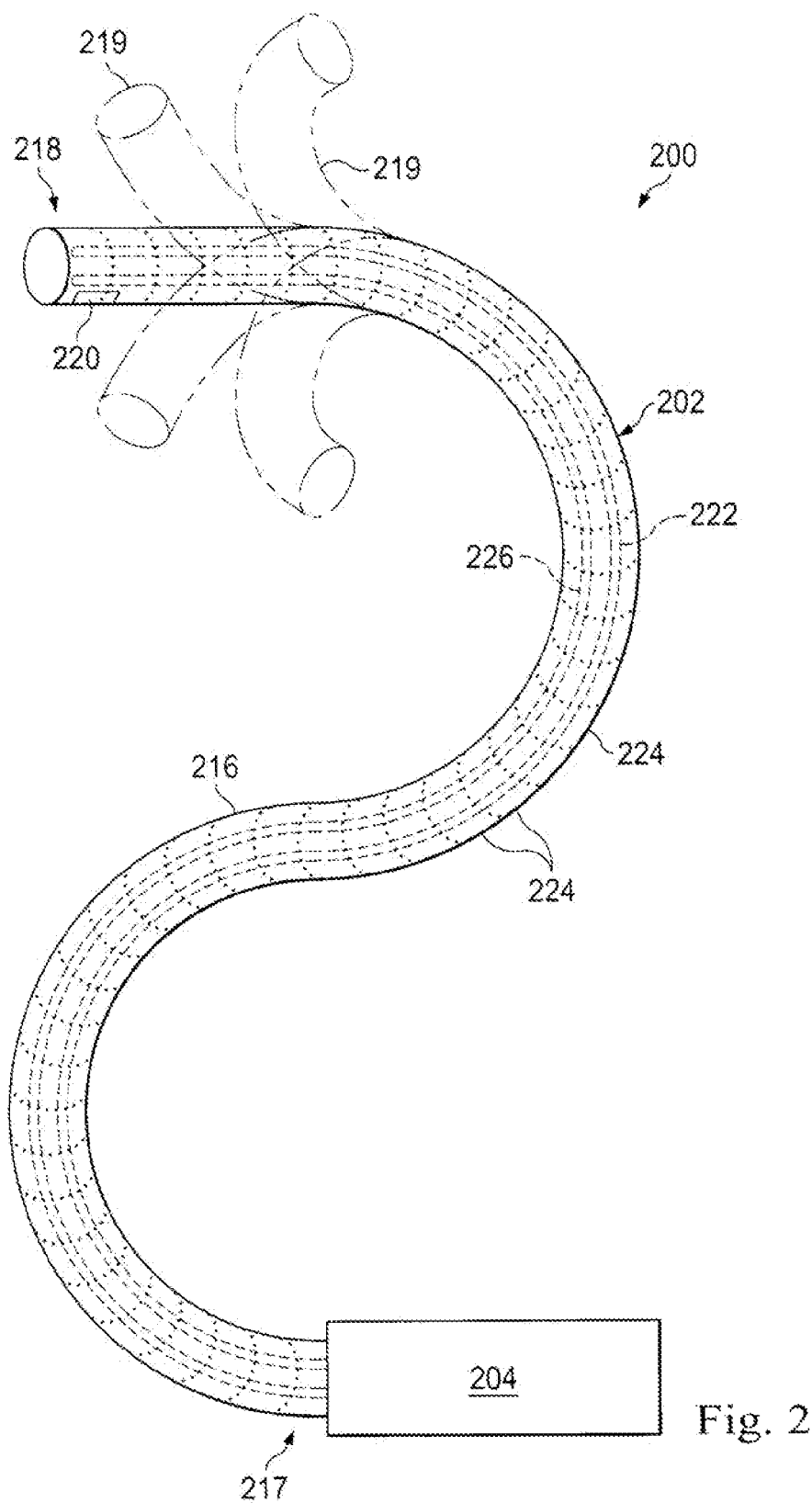
FIG. 2 illustrates a medical instrument system using aspects of this disclosure.

FIG. 2 illustrates a medical instrument system 200, which may be used as the medical instrument system 104 of teleoperational medical system 100. Alternatively, the medical instrument system 200 may be used for non-teleoperational exploratory procedures or in procedures involving traditional manually operated medical instruments, such as manual endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller, suitable for insertion in various anatomical passages. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system that interrogates the shape sensor and processes the received shape data to produce an indication of the shape of all or a portion of body 216.

The shape sensor system 222 may include an optical fiber aligned with the flexible catheter body 216 (e.g., provided within an interior channel (not shown) or mounted externally). In one embodiment, the optical fiber has a diameter of approximately 200 µm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fiber Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary, or each core may be contained in a separate optical fiber.

In some embodiments, an array of FBGs is provided within each core. Each FBG comprises a series of modulations of the core's refractive index so as to generate a spatial periodicity in the refraction index. The spacing may be chosen so that the partial reflections from each index change add coherently for a narrow band of wavelengths and therefore reflect only this narrow band of wavelengths while passing through a much broader band. During fabrication of the FBGs, the modulations are spaced by a known distance, thereby causing reflection of a known band of wavelengths. When a strain is induced on the fiber core, however, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBGs produce a reflected wavelength that is a function of the strain on the fiber and its temperature. This FBG technology is commercially available from a variety of sources, such as Smart Fibres Ltd. of Bracknell, England. Use of FBG technology in position sensors for teleoperational surgery is described in U.S. Pat. No. 7,930,065 (filed Jul. 20, 2006) (disclosing "Robotic Surgery System Including Position Sensors Using Fiber Bragg Gratings"), which is incorporated by reference herein in its entirety. The optical fiber may be used to monitor the shape of at least a portion of the catheter system 202. More specifically, light passing through the optical fiber is processed to detect the shape of the catheter system 202 and to utilize the shape information to assist in surgical procedures. The sensor system (e.g., sensor system 108) may include an interrogation system for generating and detecting the light used for determining the shape of the catheter system 202. This information, in turn, can be used to determine other related variables, such as velocity and acceleration of the parts of a medical instrument system. The sensing may be limited only to the degrees of freedom that are actuated by the teleoperational system, or it may be applied to both passive (e.g., unactuated bending of the rigid members between joints) and active (e.g., actuated movement of the instrument) degrees of freedom.

The medical instrument system may optionally include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

The flexible catheter body 216 includes a channel sized and shaped to receive an auxiliary instrument 226. Auxiliary instruments may include, for example, image capture probes, biopsy instruments, laser ablation fibers, or other surgical, diagnostic, or therapeutic tools. Auxiliary instruments may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the auxiliary instrument 226 may be an image capture probe that includes a distal portion with a stereoscopic or monoscopic camera at or near the distal end 218 of the flexible catheter body 216 for capturing images (including video images) that are processed for display. The image capture probe may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in one or more of the visible, infrared, or ultraviolet spectrums.

The flexible catheter body 216 may also house cables, linkages, or other steering controls (not shown) that extend between the instrument body 204 and the distal end 218 to controllably bend the distal end 218 as shown, for example, by the broken dashed line depictions 219 of the distal end. In embodiments in which the instrument system 200 is actuated by a teleoperational assembly, the instrument body 204 may include drive inputs that removably couple to and receive power from motorized drive elements of the teleoperational assembly. In embodiments in which the instrument system 200 is manually operated, the instrument body 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

Figure 3:
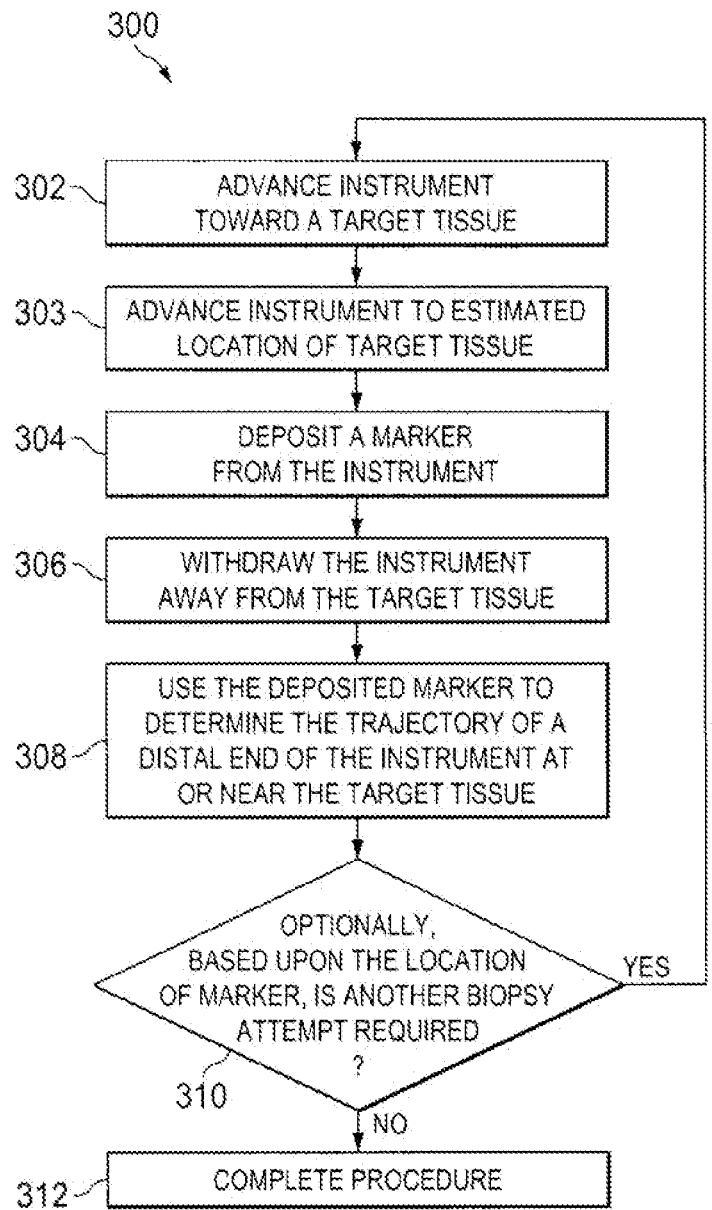
FIG. 3 illustrates a method for confirming a medical procedure according to an embodiment of this disclosure.
Figure 4:
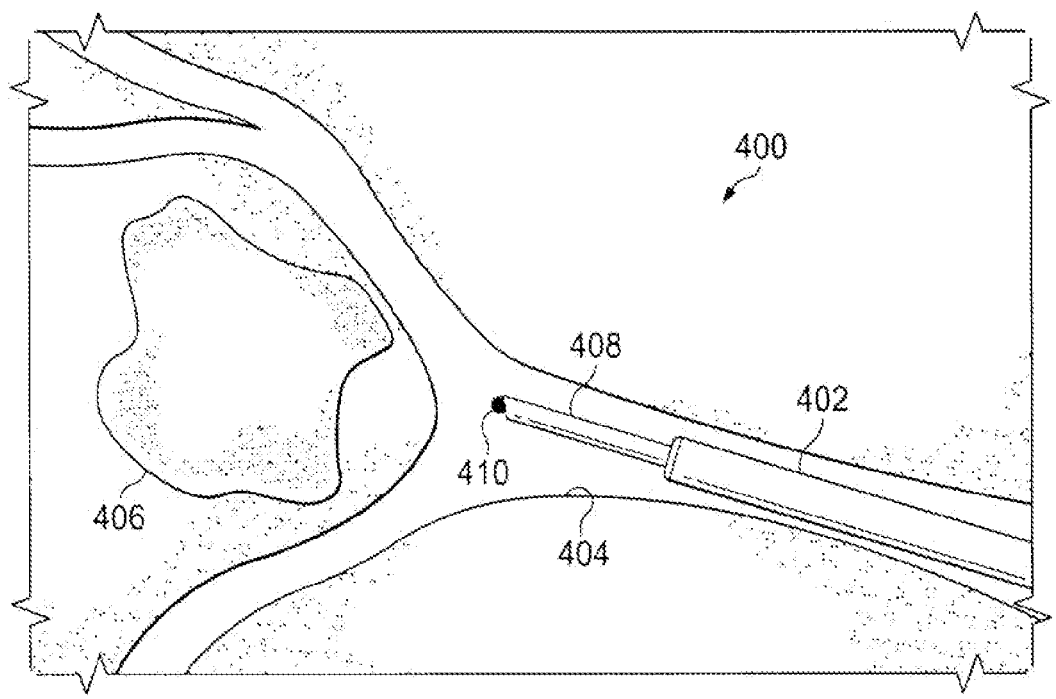
FIGS. 4-5 illustrate a biopsy procedure according to an embodiment of this disclosure.
Figure 5:
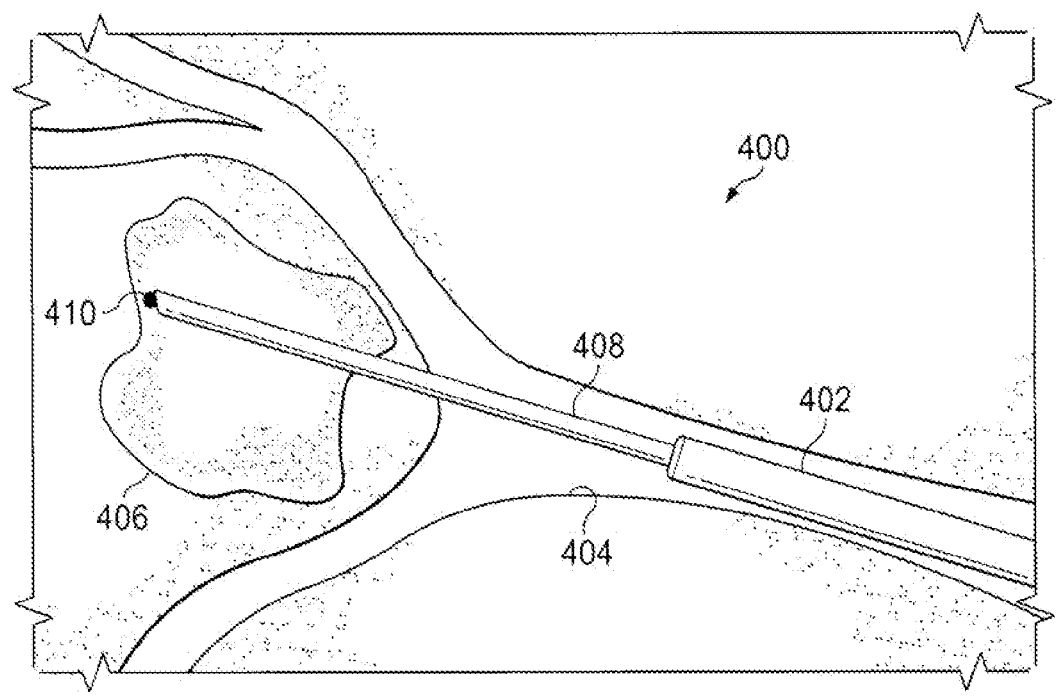
Figure 6:
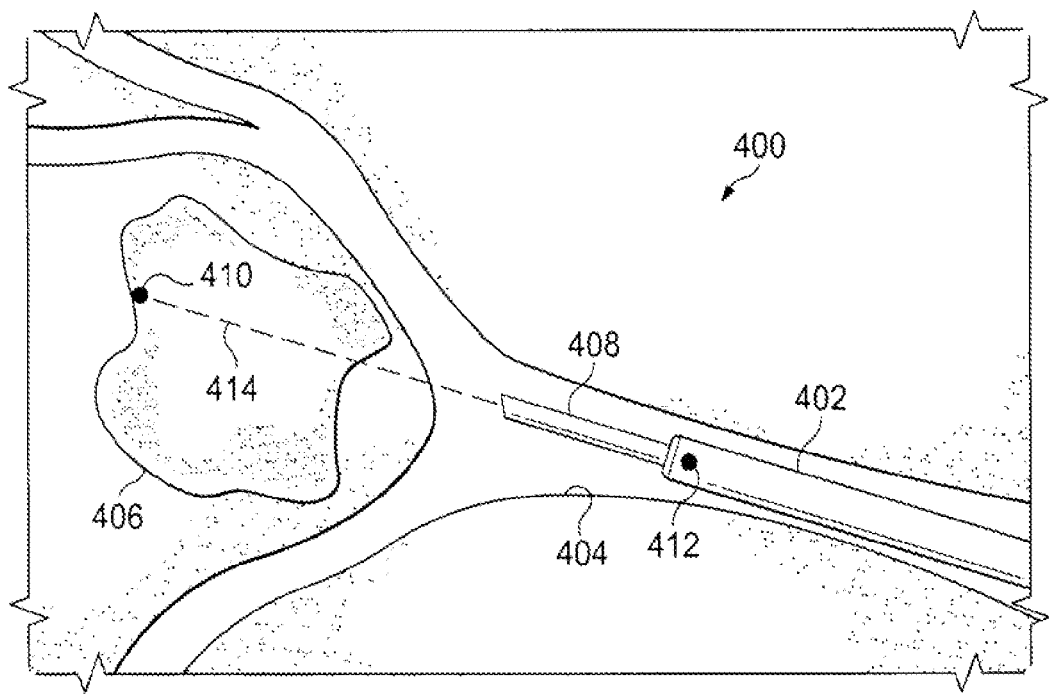
FIGS. 6-10 illustrate the use of trajectory indication devices according to various embodiments of this disclosure.

The catheter system 202 or other known medical systems, including other biopsy systems, treatment delivery systems, and implantation systems may be used in procedures requiring extreme accuracy in accessing a small (e.g., sub-centimeter) target tissue. FIG. 3 illustrates a method 300 for confirming a medical procedure, in accordance with one embodiment of this disclosure. The method 300 generally describes a confirmation technique used in a biopsy procedure, but the confirmation techniques described herein may be used in any of a variety of procedures, including treatment delivery and implantation procedures. FIGS. 4-6 also illustrate aspects of the illustrative biopsy procedure.

At 302, the method 300 includes advancing a catheter toward a target tissue. FIG. 4 illustrates a catheter 402 extending within an anatomical passageway 404 and advanced toward a target tissue 406. An elongated biopsy instrument 408 is extendable from the catheter 402 toward the target tissue 406. A marker 410 is removably coupled to the instrument 408. As shown in FIG. 5, the instrument 408 is advanced from the catheter 402 and accesses the target tissue 406. The instrument 408 may extend into or through the target tissue 406 to retrieve a sample of the tissue. The instrument 408 may have any biopsy collection configuration known in the art, including a distal end collection port, a side-opening collection port, a tissue severing mechanism, or other known biopsy tool features.

Referring again to FIG. 3, at 303 the instrument 408 is advanced to a location estimated to be in the target tissue 406 or estimated to be sufficiently into the target tissue to obtain a suitable sample of the target tissue.

At 304, the marker is deposited from the instrument in or near the target tissue. As shown in FIG. 6, the marker 410 is deposited from the instrument 408 into the target tissue 406. In this embodiment, the marker 410 may be a single seed or otherwise point-like fiducial marker. The marker may serve as a fiducial feature indicating the farthest penetration depth of the biopsy instrument. When imaged or otherwise sensed, the location of the marker may indicate if the biopsy instrument effectively sampled the target tissue, failed to reach the target tissue, or extended beyond the target tissue to obtain the sample.

At 308, the deposited marker is also used to determine the trajectory of the distal end of the biopsy instrument at or near the target tissue. Various techniques are described below for determining the trajectory and using the trajectory to confirm the success of the biopsy procedure. At 310, optionally, the trajectory may be used to determine if another biopsy attempt is required. If additional biopsy is needed, the steps 302-310 are repeated until a successful biopsy is confirmed. At 312, the procedure is then completed.

A variety of techniques may be used to determine the trajectory of the instrument 408 in and near the target tissue 406. Referring again to FIG. 6, the marker 410 may be deposited at or near the distal-most extension of the distal end of the instrument 408. A proximal marker 412 may be located at a distal tip of the catheter 402. The proximal marker 412 at the distal tip of the catheter 402 serves as an approximation of another point on the trajectory 414 of the instrument 408 as it is advanced into the target tissue. The two markers 410, 412 may be imaged or otherwise sensed. The two markers 410, 412 serve as a trajectory indication device in that the linear path between the two markers may estimate the trajectory 414 of the advanced biopsy instrument. Further description of the markers and techniques for sensing the markers will be provided in detail below. Because the biopsied tissue is removed from the anatomy along the trajectory or immediately adjacent to the trajectory, knowledge of the instrument trajectory indicates to a clinician whether the biopsy was successful. If the trajectory extends into the target tissue, the clinician will have a high degree of confidence that the target tissue was successfully biopsied. If the trajectory bypasses the target tissue, does not reach the target tissue, or substantially overextends the target tissue, then a clinician can quickly determine that additional biopsy may be required.

Figure 7:
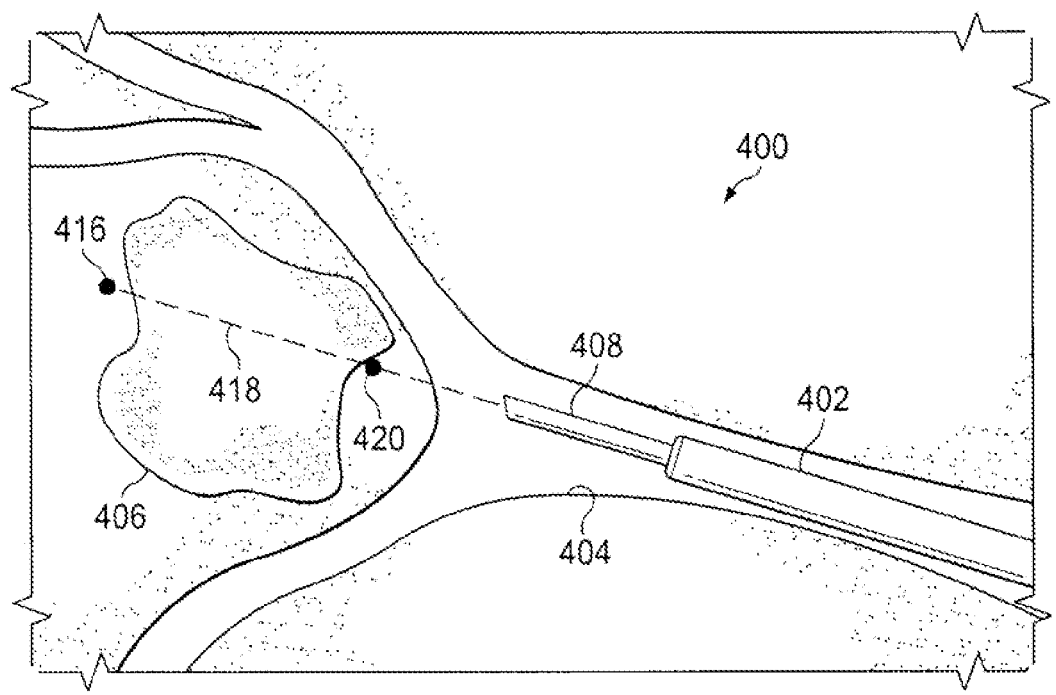

FIG. 7 illustrates an alternative technique for determining the trajectory of the biopsy instrument 408. In this embodiment, a distal marker 416 is deposited from the biopsy instrument 408 at a distal location along the instrument trajectory 418. A proximal marker 420 is deposited from the biopsy instrument 408 at another location along the instrument trajectory 418. The two markers 416, 420 may be imaged or otherwise sensed to estimate the trajectory 418 of the advanced instrument. The markers 416, 420 thus serve as a trajectory indication device for determining if the biopsy was successful (i.e., that the trajectory passed into or through the tissue targeted for biopsy, or how close the trajectory came to a center of the tissue targeted for biopsy) or should be repeated. Additional markers may also be deposited along the trajectory. Such additional markers may be used, for example, to estimate the trajectory of a curved biopsy instrument or any other biopsy procedure in which the instrument follows a non-linear, three-dimensional path.

Figure 8:
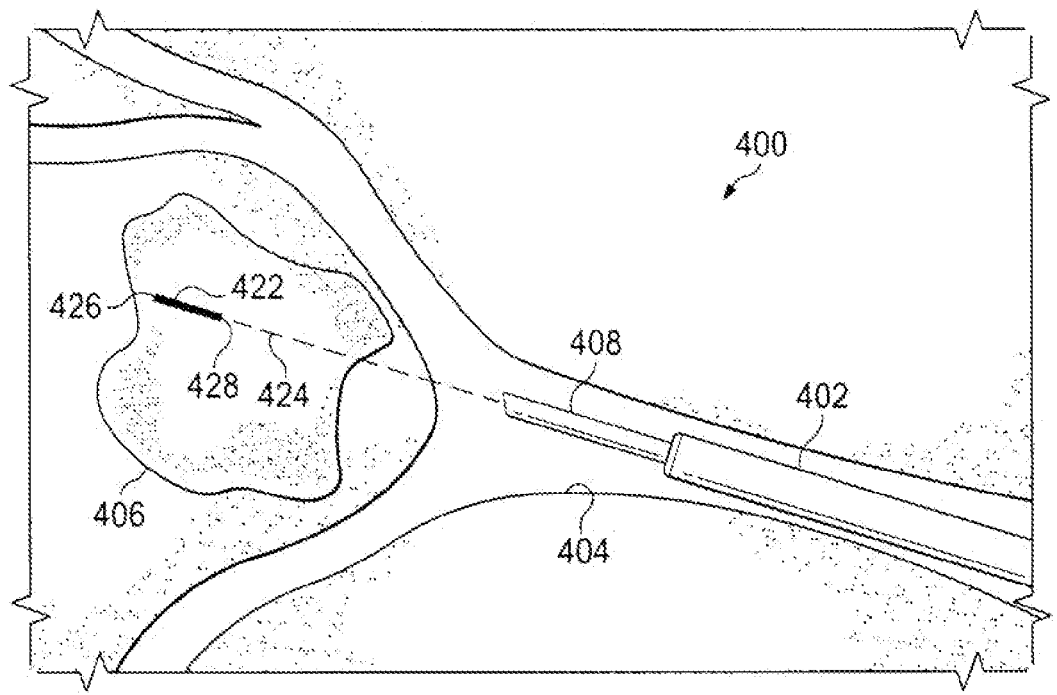

FIG. 8 illustrates an alternative technique for determining the trajectory of the instrument 408. In this embodiment the marker is an elongated marker 422 deposited from the instrument 408 along the instrument trajectory 424. As compared to the marker 410, the marker 422 is longer and visible in two dimensions when imaged or otherwise sensed. The marker 422 has a distal portion 426 linearly aligned with a proximal portion 428. Therefore, the single elongated marker 422 by itself may be used to estimate the trajectory 414 of the advanced instrument. The marker 422 thus serves as a trajectory indication device for determining if the biopsy was successful or should be repeated.

Figure 9:
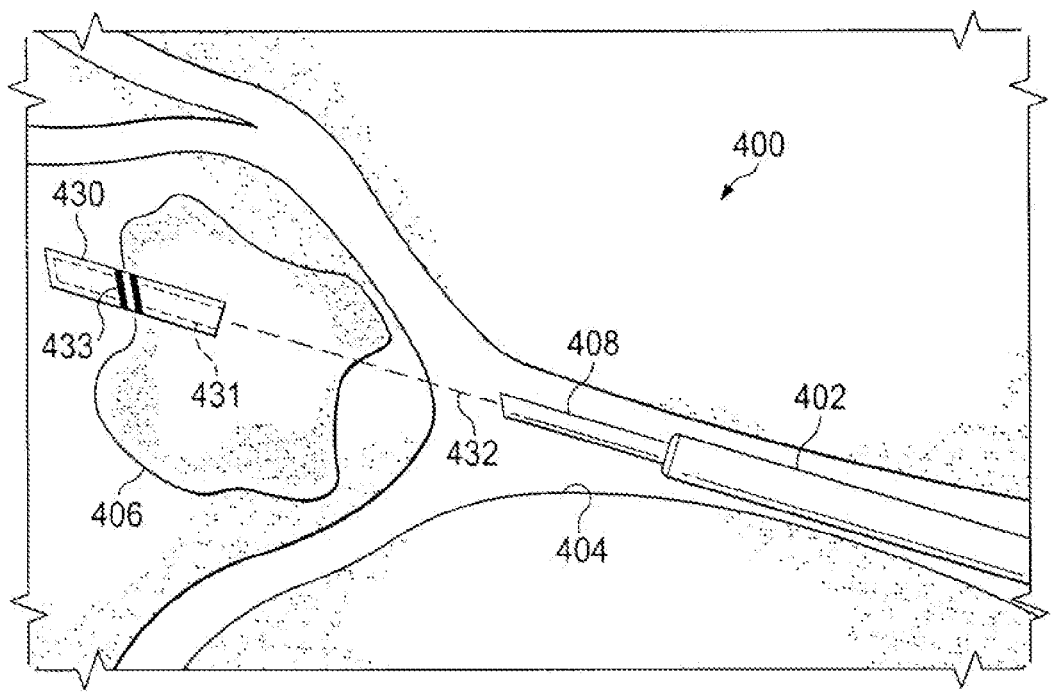

FIG. 9 illustrates an alternative technique for determining the trajectory of the instrument 408. In this embodiment, the marker is a sheath marker 430 that includes a channel 431 through which at least a portion of the instrument 408 extends as the instrument is advanced toward the target tissue 406. As the instrument 408 is retracted back into the catheter 402 during or after the biopsy procedure, the sheath marker 430 slides away from the instrument and is deposited along the trajectory 432 of the instrument. The sheath marker 430 is visible in two dimensions when imaged or otherwise sensed. Thus, the orientation of the sheath marker 430 may be used to estimate the trajectory of the instrument. Accordingly, the marker 430 serves as a trajectory indication device for determining if the biopsy was successful or should be repeated.

Figure 10:
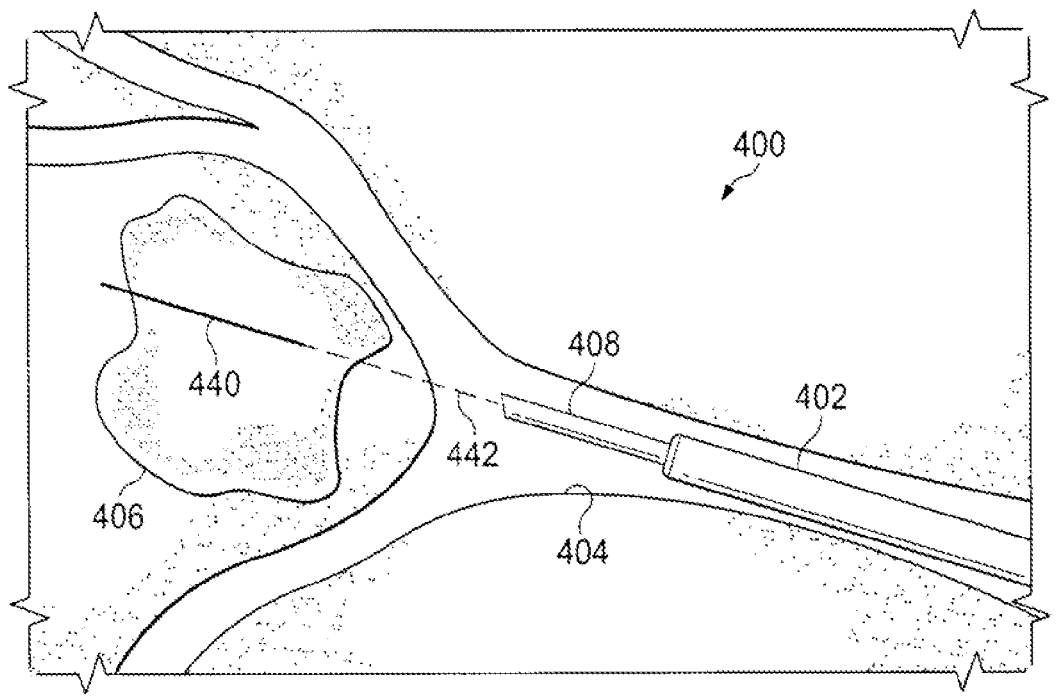

FIG. 10 illustrates an alternative technique for determining the trajectory of the instrument 408. In this embodiment, the marker is a trailing material 440 deposited from the instrument 408 along the trajectory 442. The trailing material 440 is visible in two dimensions when imaged or otherwise sensed. Thus, the orientation of the trailing material 440 may be used to estimate the trajectory of the instrument and the successfulness of the procedure. The trailing material may be, for example, a flexible filament or thread that is unfurled from the instrument along the trajectory. In another alternative, the trailing material may be a liquid marking agent, such as a dye, that is deposited from the instrument along the trajectory.

Figure 11:
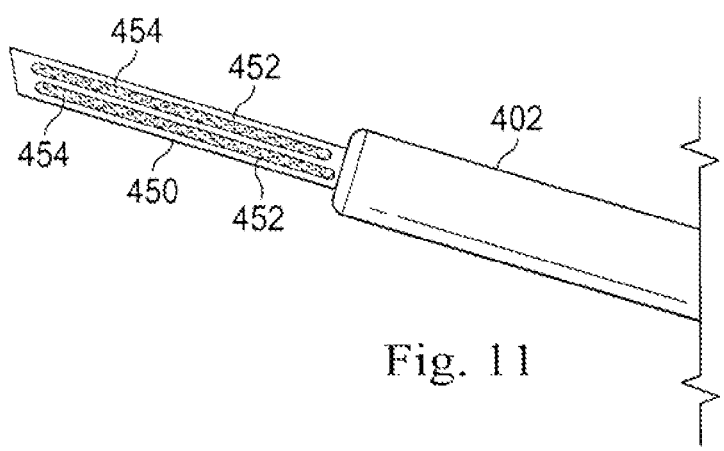
FIG. 11 illustrates an instrument system including a trajectory indication device according to another embodiment of this disclosure.

FIG. 11 illustrates a configuration for passively delivering a marking agent. In this embodiment, an instrument 450 includes one or more material holders 452 for retaining a marking agent 454. The marking agent may be, for example, a liquid (e.g., a fluorescent dye), a solid (e.g., a chalk-like substance), or a gel. The material holder 452 may be a groove, a series of indentations, an absorbent strip, or any other device for containing the marking agent or adhering the marking agent to the instrument 450. As the instrument 450 and marking agent 454 move through tissue, the marking agent is frictionally dislodged from the material holder 452 and becomes deposited on the tissue along the trajectory of the instrument. In alternative embodiments, a marking agent may be distributed by an active delivery system such as a pump.

Markers in accordance with aspects of the invention exist in various forms or combinations of forms. Any of the markers, including marking agents, may be active—meaning they emit energy that is detectable by an imaging system. Examples of active markers include radioactive or ultrasonic markers. Similarly, one or more portions of a single marker may be active, so that a single marker with two or more active features can be used to indicate an instrument's trajectory. Alternatively, any of the markers, including marking agents, may be passive—meaning they require external energy for imaging or sensing. For example, a radiopaque marker is a passive marker that that may be detected when imaged with X-ray technology, such as CT imaging. Another type of passive marker may include an EM sensor. Yet another example of a passive marker is a marker with one or more radiolucent features or symbols, so that a single radiopaque elongate marker with radiolucent features at either end would serve to indicate an instrument's trajectory, for example. A marker may include a polymer material, a metal, a ceramic material, or other suitable biocompatible material for creating a solid, liquid, gel, or other detectable substance. A marker may include active or passive identification 433 or other symbolic patterns, as shown in FIG. 9, that are detectable by external imaging or sensing systems and that serve to identify the marker and/or show its orientation. Two or more markers each having unique identifications can be distinguished from one another.

In various embodiments, a marker may be permanent—meaning it remains substantially unchanged over time (e.g., a year or more) in the anatomy. In other embodiments, the marker may be temporary—meaning it may be resorbed, expelled, or otherwise have a brief existence within the patient's body. For example, the marker may be resorbable based upon the amount of radiation it receives. Thus, a marker's presence or size may indicate the dose of radiation received by the marker and the surrounding tissue. In this example, a completely resorbed marker may indicate that a sufficient total dosage of radiation has been received during multiple treatment sessions. Alternatively, the marker may be permanent but may become altered in an externally detectable manner to indicate the amount of radiation received.

In various embodiments, the marker may be a bio-marker that changes in response to received energy, such as radiation or that changes in response to the chemistry of the adjacent tissue. For example, the marker may react in a detectable manner to cancerous tissue. With a bio-marker, the change indicator may be visible (e.g., fluorescence), radiological (e.g., radiopacity), or physiological (e.g., temperature or density). Alternatively, a bio-marker may be responsive to the surrounding tissue such that upon detection of predetermined properties of the surrounding tissue, the bio-marker may undergo a physical or chemical change that treats the surrounding tissue or causes it to become detectable by a sensor, including an imaging system.

In various embodiments, the marker may be anchorable to the surrounding tissue so that the marker does not move between implantation and biopsy confirmation. The anchoring of the marker may be robust enough to maintain the position of the marker through a subsequent treatment plan, such as radiation therapy. The anchored marker may thus serve as a guide to direct the location of radiation therapy.

In various embodiments, the marker may function as a sensor. For example, if a small, sub-centimeter lesion is not clearly visible with an imaging system, the implanted marker may sense information about the surrounding tissue and send the sensed data wirelessly to an external receiver for processing and diagnosis. For example, the marker may provide microscopic sensing by using visible light imaging or OCT-like imaging. With these techniques an optical biopsy may be performed.

In various embodiments, a marker may be externally manipulated (e.g., by magnetic or wireless remote control) to traverse an area of the tissue to reach a target location. After the marker is moved to the target location, the detected marker can serve as an indication of target tissue location so that treatment, such as radiation or surgery, may be directed toward the marker.

In various embodiments, the marker may include a miniature source of x-rays (e.g., a carbon nanotube-based field emission x-ray source) that can provide a localization signal. An array of such markers may be used to radiographically image the local onto an internally or externally positioned x-ray detector In an exemplary embodiment, several sub-centimeter diameter tissues of interest may be identified in lung tissue using, for example, CT imaging. An actively guided biopsy probe (e.g., catheter system 202) may be guided to the location of each tissue of interest where a tissue sample may be taken. The probe deposits a marker as previously described. When the biopsy procedure for each tissue of interest is complete, all of the biopsy locations are imaged. The markers and/or marked trajectories are identified. If the post-biopsy images indicate that biopsy at any location failed to collect a proper sample, a second biopsy may be attempted at that location. A second marker may be used to indicate the second biopsy location and trajectory. If a biopsy failure is determined soon after an initial attempt, a second attempt can be made within the context of a single patient biopsy surgical procedure so that clinic resources may be maximized and patient discomfort minimized.

In another exemplary embodiment, the marked trajectory may be used to re-navigate the original trajectory to deliver a treatment to the target tissue. For example, if the confirmation procedure confirms that the target tissue was accessed, and if biopsy analysis indicates that treatment is indicated, then the deposited marker(s) may provide guidance to a clinician to return with a treatment instrument to the location of the target tissue to direct treatment. As one example, a treatment instrument may be guided to the location of the original marker to deliver a radioactive seed for treatment of the target tissue.

In another exemplary embodiment, the marker may be carried to the target tissue using an initial scouting instrument. The initial scouting instrument deposits the marker, and the scouting instrument is removed. After the marker and/or the trajectory of the scouting instrument are evaluated to determine that the target tissue has been marked, a separate biopsy instrument may be advanced to the location of the marker to conduct the biopsy procedure. In this embodiment, the scouting instrument and the biopsy instrument may be advanced through a catheter, which may remain in the anatomy after the scouting instrument has been removed and may subsequently receive the biopsy instrument.

In another exemplary embodiment, a catheter guide may be omitted. The biopsy needle or another type of treatment tool may carry the marker to the target location and conduct the biopsy or other type of treatment without use of a catheter guide. For example, the natural anatomic passageway of the patient may provide the necessary guidance to a target tissue located in or in the near proximity of the anatomic passageway.

One or more elements in the described embodiments may be implemented in software to execute on a processor of a computer system, such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks, such as the Internet, an intranet, etc.

The processes and displays described herein may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the inventive aspects described herein.

While certain exemplary embodiments of the invention have been described and shown in the accompanying drawings, it is to be understood that such embodiments are merely illustrative of and not restrictive on the broad inventive aspects, and that the embodiments of the invention not be limited to the specific constructions and arrangements shown and described, since various other modifications may occur to those ordinarily skilled in the art.

What is claimed is:

1. A method comprising:
   advancing a medical instrument and a catheter toward a target tissue within a patient anatomy, the medical instrument including a distal sheath marker and slidably received within the catheter, the distal sheath marker including a channel and an identification feature, wherein at least a portion of the medical instrument is slidably received within the channel;
   depositing the distal sheath marker at a location at or near the target tissue, wherein the distal sheath marker indicates a farthest advancement point of the medical instrument within the patient anatomy;
   after the depositing of the distal sheath marker, withdrawing the medical instrument away from the target tissue;
   determining an orientation of the distal sheath marker based on the identification feature; and
   after the withdrawing of the medical instrument, using the location and the determined orientation of the deposited distal sheath marker to determine a trajectory of a distal end of the medical instrument at or near the target tissue.

2. The method of claim 1 further comprising removing a biopsy sample from the target tissue.

3. The method of claim 1 wherein the distal sheath marker includes an energy emitting component.

4. The method of claim 1 wherein the distal sheath marker includes a radiopaque component.

5. The method of claim 1 wherein the distal sheath marker includes a component that undergoes a physical alteration if tissue at the location at or near the target tissue is diseased.

6. The method of claim 1 wherein the trajectory is a linear trajectory.

7. The method of claim 1 further comprising using the trajectory of the distal end of the medical instrument to determine that the medical instrument and the catheter should be advanced toward the target tissue along a second trajectory.

8. The method of claim 1, wherein the identification feature includes an energy emitting component.

9. The method of claim 1, wherein the identification feature includes a radiopaque component.

10. The method of claim 1, wherein the identification feature includes a plurality of identification markers arranged in a pattern.

11. A system comprising:
    an elongated instrument;
    a catheter sized to slidably receive the elongated instrument; and
    a trajectory indication device including a distal sheath marker, the trajectory indication device configured to indicate a trajectory of a distal end of the elongated instrument at or near a target tissue in a patient anatomy, the trajectory indication device configured to be deposited in a location at or near the target tissue, the trajectory indication device indicating a farthest advancement point of the elongated instrument within the patient anatomy, the trajectory indication device including:
a channel, wherein at least a portion of the elongated instrument is configured to be slidably received within the channel; and
an identification feature configured to indicate an orientation of the trajectory indication device.

12. The system of claim 11 wherein the identification feature includes an energy emitting component.

13. The system of claim 11 wherein the identification feature includes a radiopaque component.

14. The system of claim 11 wherein the trajectory indication device includes a component that undergoes a physical alteration if the target tissue in the patient anatomy is diseased.

15. The system of claim 11, wherein the elongated instrument is configured to remove a biopsy sample from the target tissue.

16. The system of claim 11 wherein the trajectory is a linear trajectory.

17. The system of claim 11, wherein the trajectory indication device is further configured to indicate that the elongated instrument and the catheter should be advanced toward the target tissue along a second trajectory.

18. The system of claim 11, wherein the identification feature includes a plurality of identification markers arranged in a pattern.

* * * * *